United States Patent [19]

Whittenberger et al.

[11] 4,452,088
[45] Jun. 5, 1984

[54] METHOD AND APPARATUS FOR GRIPPING UNIAXIAL FIBROUS COMPOSITE MATERIALS

[75] Inventors: John D. Whittenberger, North Olmsted; Frances I. Hurwitz, Shaker Heights, both of Ohio

[73] Assignee: The United States of America as represented by the Administrator of the National Aeronautics and Space Administration, Washington, D.C.

[21] Appl. No.: 418,139

[22] Filed: Sep. 15, 1982

[51] Int. Cl.³ .......................... G01N 3/04; G01N 3/08
[52] U.S. Cl. .......................................... 73/856; 73/833
[58] Field of Search .................. 73/856, 860, 831, 833

[56] References Cited

U.S. PATENT DOCUMENTS

| 1,943,931 | 1/1934 | Ruch | 24/365 |
|---|---|---|---|
| 2,419,711 | 4/1947 | Dillon | 24/263 |
| 2,676,381 | 4/1954 | Holmes | 73/831 |
| 3,224,259 | 12/1965 | De Nicola | 73/103 |

OTHER PUBLICATIONS

N. R. Adsit "Some Experiences in Elevated Temperature Testing of Graphite-Reinforced Composite Materials" Book II; vol. 24, pp. 829–838; 24th SAMPE 1979. Whittenberger & Hurwitz "Application of a Gripping System to Test a Uniaxial Graphite Fiber Reinforced Composite (PMR 15/Celion 6000) in Tension at 316° C."; vol. 3, No. 2, Apr. 1982, M. Sittig "Carbon and Graphite Fibers" Noyes Data Corporation; 1980; pp. 334–335.

Primary Examiner—Anthony V. Ciarlante
Attorney, Agent, or Firm—Norman T. Musial; John R. Manning; Gene E. Shook

[57] ABSTRACT

A strip specimen is cut from a unidirectional strong, brittle fiber composite material, and the surfaces of both ends of the specimen are grit-blasted. The specimen is then placed between metal load transfer members having grit-blasted surfaces. Sufficient compressive stress is applied to the load transfer members to prevent slippage during testing at both elevated temperatures and room temperatures.

5 Claims, 1 Drawing Figure

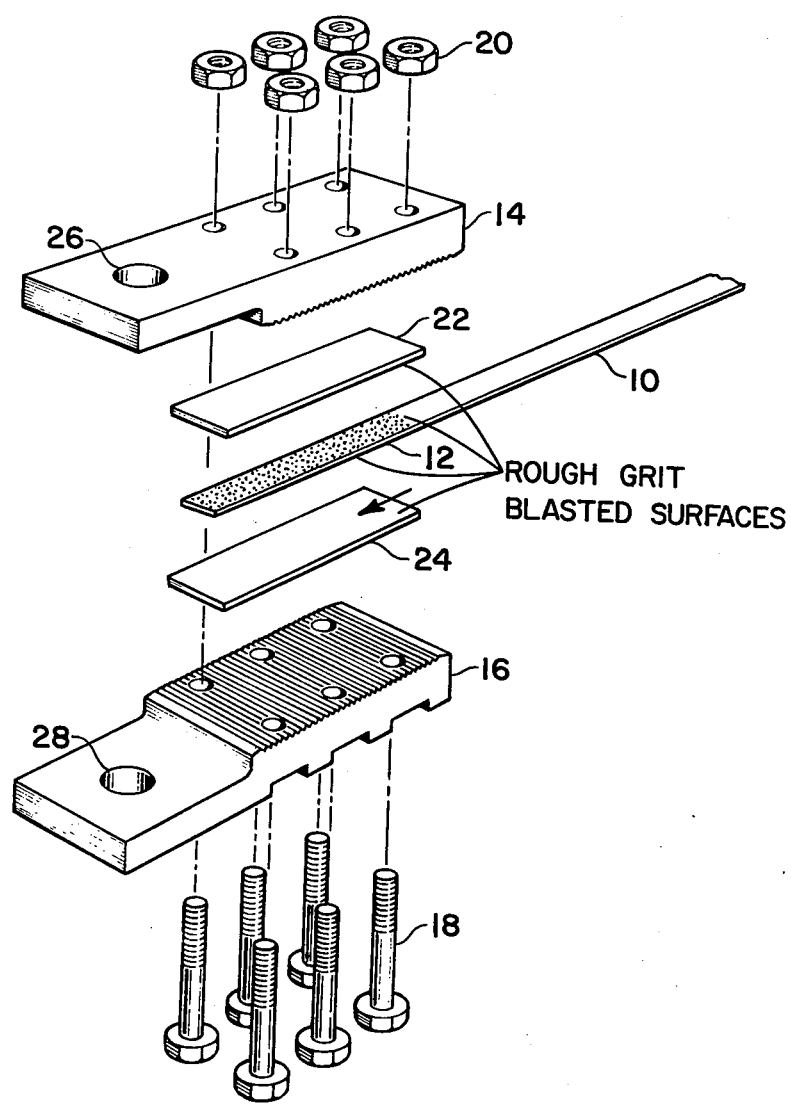

METHOD AND APPARATUS FOR GRIPPING UNIAXIAL FIBROUS COMPOSITE MATERIALS

DESCRIPTION

ORIGIN OF THE INVENTION

The invention described herein was made by employees of the United States Government and may be manufactured and used by or for the Government for governmental purposes without the payment of any royalties thereon or therefor.

TECHNICAL FIELD

This invention is concerned with gripping brittle test specimens that are both strong and slippery. The invention further provides improved gripping to facilitate mechanical property testing at elevated temperatures. This gripping is particularly directed to testing the mechanical properties of unidirectional fiber laminates over a wide range of temperatures using simple test specimen geometries.

While measurement of short and long term tensile properties is routine for materials like metal matrix composites, brittle matrix-strong, brittle fiber composites pose a more severe problem. Conventional metallic tensile specimen design and gripping techniques result in out-of-gage failures when applied to brittle matrix-strong fiber composites. These failures are due, in part, to the extreme differences in the strengths between the matrix and the fiber, the glass-like characteristics of the resin, and the slippery, bearing quality, nature of the laminate surface.

Long strip specimens that are thin and narrow have been proposed for mechanical testing. These specimens have adhesively bonded expoxy/glass tabs to avert failure in the gripping region which results from the use of conventional serrated grips. While such specimens have been satisfactory at intermediate temperatures up to about 150° C., these specimens have been unsatisfactory at more elevated temperatures above 300° C. because of softening of the epoxy/glass tabs. Also, the adhesive material is unable to transfer the load adequately between the composite specimens and the tabs. The thermoplastic-like behavior of the matrix resin also makes this type of specimen undesirable.

BACKGROUND ART

Ruch U.S. Pat. No. 1,943,931 describes a test strip that is placed between the jaws of a fixture. The faces of these jaws have serrations, file marks, or the like.

Dillon U.S. Pat. No. 2,419,711 describes a gripping device that is similar to that of the Ruch patent. This patent discloses serrated gripping faces.

DeNicola U.S. Pat. No. 3,224,259 also describes a gripping device that is similar to that of the Ruch patent. The gripping surfaces of the device shown in the DeNicola patent have teeth.

DISCLOSURE OF INVENTION

In accordance with the present invention a strip specimen is cut from a unidirectional strong, brittle fiber composite material that has been fabricated in a conventional manner. The surfaces of both ends of the test specimen are grit-blasted. This specimen is then placed in a fixture having grit-blasted metal faces on load transfer members in contact with the grit blasted surfaces.

Sufficient compressive stress is applied to the load transfer members to prevent slippage during testing at both elevated temperatures and room temperatures. Adhesives, load pads, and other secondary composite processing are not required. This gripping system has been successful in tensile testing, creep-rupture testing, and fatigue testing uniaxial composite materials at 316° C.

BRIEF DESCRIPTION OF THE DRAWINGS

The details of the invention will be described in connection with the accompanying drawing which is a perspective view of gripping apparatus constructed in accordance with the present invention.

BEST MODE FOR CARRYING OUT THE INVENTION

Referring now to the drawing there is shown a strip specimen 10 that has been cut from a sheet of composite material that is to be tested. In order to illustrate the features of the invention, strip specimens 10 were cut from a sheet of PMR 15/Celion 6000 composite material. This uniaxial, 0° orientation material has extremely high strength and presents one of the most severe gripping problems among composite materials.

Elastic modulus, fracture stress, and strain at failure were determined for several PMR 15/Celion 6000 panels produced by the standard cold-mold process and by a hot mold process. The test results were statistically analyzed and compared with room temperature tensile properties of cold-molded laminates measured by using the traditional epoxy/glass tab system, as well as the high temperature gripping method. The invention was also used to conduct long term elevated temperature testing of PMR 15/Celion 6000 composites.

Each test specimen 10 was nominally 200 mm long, 9.5 mm wide, and 1.5 mm thick. A gripping portion 12 was located at each end of the specimen 10. Each gripping portion 12 was approximately 60 mm long.

After each test specimen 10 was cut from the sheet of composite material, each gripping portion 12 was rough grit-blasted with number 36 Alundum grit. The center section between the opposed gripping portions was protected by masking. Each test specimen 10 was then assembled into the gripping system shown in the drawing with the aid of alignment fixtures.

According to the present invention the gripping system comprises a pair of spaced grip pieces 14 and 16 adjacent to each of the gripping portions 12 of the test specimen 10. These grip pieces are preferably ferritic tool steel. A plurality of bolts 18 pass through the grip pieces 14 and 16 on either side of the gripping portion 12 of the test specimen 10. Each bolt 18 is threadably engaged by a mating nut 20 so that a predetermined compressive force can be applied to the grip pieces. These bolts and nuts are preferably ferritic tool steel or ferritic stainless steel.

A novel structural improvement in the gripping system is the provision of a load transfer member 22 between the grip piece 14 and the test specimen 10. A similar load transfer member 24 is positioned between the grip piece 16 and the test specimen 10. The load transfer members 22 and 24 are cut from metal stock which is preferably a mild steel or a nickel-base alloy. The important feature of the invention is that the surfaces of the load transfer members 22 and 24 which face the test specimen 10 are rough grit blasted in the same manner as the surfaces of the gripping portion 12. By placing the grit blasted surfaces of the load transfer members and the test specimen in frictional engagement through compression of the rough grit-blasted gripping portions 12 of the laminated test specimen 10 between grit-blasted surfaces of the metal load transfer members 22 and 24, load transfer is accomplished.

These grit-blasted/grit-blasted interfaces produce shear surfaces capable of transmitting quite high tensile loads on the order of 22 kN without initiating either premature failure or slipping. More particularly, the balance among premature failure in the grip, slipping, and true tensile fracture is delicate; thus, the torque on the bolts 18 is critical. For uniaxial PMR 15/Celion 6000 specimens with four nominally 57×9.5 mm shear surfaces being tested with a gripping system shown in the drawing, the maximum torque was 425 Nm (95 in.-lbs.) for the specimen tested at room temperature. The maximum torque for the specimen tested at 316° C. was 735 Nm (160 in.-lbs.) Torques in excess of these figures lead to premature fracture in the gripping portion during testing. The higher initial torque required for testing at 316° C. was necessitated by stress relaxation of the bolts 18 during heating.

In order to illustrate the beneficial technical effect of the gripping system, tensile tests were conducted in air in a screw-type universal testing machine which was operably connected to the gripping system by pins which pass through holes 26 and 28 in the grip pieces 14 and 16 respectively. These tests were made in accordance with the alignment, temperature control, calibration, etc. procedures for metallic materials set forth in ASTM specifications.

For tests at 316° C. the entire gripping specimen assembly was placed in a tube furnace and heated to the required temperature. The temperatures were monitored with thermocouples placed slightly above, below, and in the center of the 38 mm gauge section. During heating, a small tensile load of about 0.2 kN was maintained on each test specimen to prevent bending or compressive stresses.

The specimens were slowly heated over a period of two to three hours and maintained at 316° C. for at least half an hour prior to testing. With a few exceptions, all tests were conducted at a cross-head velocity of 0.0033 mm/s, which produced a nominal strain rate of $9.5 \times 10^{-6} s^{-1}$ within the gauge section.

No lower temperature limits for the gripping procedure should exist. However, it is contemplated that the upper use temperature is probably limited to the glass transition of the resin which is the matrix material of the composite. At this glass transition temperature the matrix softens, and it can exhibit viscous flow. At such temperature the matrix is unable to transmit load from the fiber to the grip.

The materials utilized for the load transfer members 22 and 24 and the bolts 18 can be adjusted for use at these more elevated temperatures. By way of example, tool steels and ferritic stainless steels soften at temperatures nominally above 540° C. For higher temperature applications more temperature resistant nickel-base alloys can be substituted to enable the gripping system to be utilized at temperatures up to at least 1000° C.

While the preferred embodiment of the gripping apparatus has been shown and described, it will be appreciated that various structural modifications may be made without departing from the spirit of the invention or the scope of the subjoined claims.

We claim:

1. An apparatus for tensile testing a composite material specimen having oppositely disposed surfaces grit blasted to a predetermined roughness on each end portion thereof, an improved gripping means comprising
   a pair of spaced grip members adjacent to each of said end portions of said specimen, each of said grip members facing one of said grit blasted surfaces,
   a load transfer member between each of said grip members and said specimen, said load transfer member having a face grit blasted to substantially the same roughness as said predetermined roughness of the surfaces on the end portion of said specimen for engaging said grit blasted surfaces on said specimen, and
   means for applying a predetermined compressive force to said grip members sufficient to maintain each grit blasted face of each transfer member in frictional engagement with the mating grit blasted surface on said specimen without fracturing said specimen during testing.

2. Tensile testing apparatus as claimed in claim 1 wherein the means for applying said predetermined compressive force to said grip members comprises
   a plurality of bolts tightened at a predetermined torque.

3. A method of gripping a composite material specimen for tensile testing comprising the steps of
   grit blasting oppositely disposed surfaces on opposed end portions of said specimen,
   positioning a load transfer member having a grit blasted face adjacent to each of said grit blasted surfaces, and
   applying a predetermined compressive force to said load transfer members sufficient to maintain each grit blasted face of each load transfer member in frictional engagement with the mating grit blasted surface on said specimen without fracturing said specimen during testing.

4. A method of gripping as claimed in claim 3 including the steps of
   placing a grip member in engagement with each of said load transfer members on a surface thereof opposite to said grit blasted face, and
   applying said compressive force to said grip members.

5. A method of tensile testing a composite material comprising the steps of
   cutting a strip specimen from said composite material,
   grit blasting the surfaces of said strip specimen at both ends thereof,
   positioning said strip specimen between a pair of spaced load transfer members having grit blasted faces in engagement with said grit blasted surfaces of said strip specimen,
   applying a predetermined compressive force to said load transfer member sufficient to maintain each grit blasted face of each load transfer member in frictional engagement with the adjacent grit blasted surface of said strip specimen, and
   applying a predetermined tensile loading to said load transfer members.

* * * * *

UNITED STATES PATENT OFFICE
CERTIFICATE OF CORRECTION

PATENT NO. : 4,452,088
DATED : June 5, 1984
INVENTOR(S) : John D. Whittenberger et al It is certified that error appears in the above-identified patent and that said Letters Patent are hereby corrected as shown below:

Column 4, line 4, cancel "An" and insert --In--

Signed and Sealed this

Sixth Day of November 1984

[SEAL]

Attest:

GERALD J. MOSSINGHOFF

Attesting Officer

Commissioner of Patents and Trademarks